US010550046B2

(12) United States Patent
Suzuki et al.

(10) Patent No.: US 10,550,046 B2
(45) Date of Patent: Feb. 4, 2020

(54) CATALYST FOR ISOBUTYLENE PRODUCTION AND METHOD FOR PRODUCING ISOBUTYLENE

(71) Applicant: Mitsubishi Chemical Corporation, Chiyoda-ku (JP)

(72) Inventors: Tatsuya Suzuki, Chiyoda-ku (JP); Akio Takeda, Chiyoda-ku (JP); Toshiya Yasukawa, Chiyoda-ku (JP); Wataru Ninomiya, Chiyoda-ku (JP); Ken Ooyachi, Chiyoda-ku (JP)

(73) Assignee: Mitsubishi Chemical Corporation, Chiyoda-ku (JP)

( * ) Notice: Subject to any disclaimer, the term of this patent is extended or adjusted under 35 U.S.C. 154(b) by 0 days.

(21) Appl. No.: 15/553,869

(22) PCT Filed: Apr. 20, 2016

(86) PCT No.: PCT/JP2016/062529
§ 371 (c)(1),
(2) Date: Aug. 25, 2017

(87) PCT Pub. No.: WO2016/171178
PCT Pub. Date: Oct. 27, 2016

(65) Prior Publication Data

US 2018/0072636 A1 Mar. 15, 2018

(30) Foreign Application Priority Data

Apr. 22, 2015 (JP) ................................ 2015-087604

(51) Int. Cl.
*C07C 1/24* (2006.01)
*B01J 21/04* (2006.01)
*B01J 35/10* (2006.01)
*C01F 7/02* (2006.01)

(52) U.S. Cl.
CPC ................ *C07C 1/24* (2013.01); *B01J 21/04* (2013.01); *B01J 35/1019* (2013.01); *C01F 7/02* (2013.01); *C01P 2006/12* (2013.01); *C07C 2521/04* (2013.01)

(58) Field of Classification Search
CPC .......... B01J 21/04; B01J 35/1019; C01F 7/02; C01P 2006/12; C07C 1/24; C07C 2521/04; C07C 11/08
See application file for complete search history.

(56) References Cited

U.S. PATENT DOCUMENTS

| | | | | |
|---|---|---|---|---|
| 5,475,183 A * | 12/1995 | Araki | B01J 21/04 585/638 |
| 9,758,442 B2 * | 9/2017 | Chaumonnot | B01J 21/12 |
| 2015/0057481 A1 | 2/2015 | Chaumonnot et al. | |
| 2015/0361007 A1 | 12/2015 | Millet et al. | |

FOREIGN PATENT DOCUMENTS

| | | |
|---|---|---|
| JP | 04-247043 | 9/1992 |
| JP | 2013-506717 A | 2/2013 |
| JP | 2013-516487 A | 5/2013 |
| JP | 2013-522270 A | 6/2013 |
| WO | 2011/085223 A1 | 7/2011 |
| WO | 2014/118484 A1 | 8/2014 |

OTHER PUBLICATIONS

International Search Report dated Jul. 12, 2016, in PCT/JP2016/062529 filed Apr. 20, 2016.
Lili Zhang et al., Chemical Reaction Engineering and Technology, Apr. 2013, vol. 29, No. 2, p. 176-180.
Lili Zhang et al., Specialty Petrochemicals, Mar. 2013, vol. 30, No. 2, p. 17-21.
Richard G. Herman et al., "Dehydrocondensation of alcohols to form ethers over mesoporous SBA-15 catalyst", Journal of Catalysis, Oct. 2004, vol. 228, p. 347-361.
Vendelin Macho et al., "Dehydration of $C_4$ alkanols conjugated with a positional and skeletal isomerization of the formed $C_4$ alkenes", Applied Catalysis A, General, Jun. 2001, vol. 214, p. 251-257.
Vendelin Macho et al., "Skeletal isomerization of n-butenes present in $C_4$ pyrolysis residue fraction", Applied Catalysis A, General, Jan. 2000, vol. 203, p. 5-14.
Joshua D. Taylor et al., "Dehydration of Fermented Isobutanol for the Production of Renewable Chemicals and Fuels", Topics in Catalysis, May 2010, vol. 53, p. 1224-1230.

* cited by examiner

*Primary Examiner* — Sharon Pregler
(74) *Attorney, Agent, or Firm* — Oblon, McClelland, Maier & Neustadt, L.L.P.

(57) ABSTRACT

Provided are: a catalyst for dehydration, with which isobutylene is able to be produced with high conversion and high selectivity through a dehydration reaction of isobutanol; and a method for producing isobutylene. This catalyst has a BET specific surface area within the range of from 210 $m^2/g$ to 350 $m^2/g$ (inclusive) as calculated from $N_2$ adsorption/desorption isotherms. It is preferable that this catalyst is formed of at least one substance selected from among alumina, silica alumina, zeolite, and solid phosphoric acid. It is more preferable that this catalyst contains alumina, and it is especially preferable that this catalyst is formed of alumina. In this method for producing isobutylene, the isobutanol concentration in the starting material gas is preferably 20% by volume or more, more preferably 40% by volume or more, and especially preferably 60% by volume or more. In addition, the temperature of a catalyst layer is preferably from 230° C. to 370° C. (inclusive), and more preferably from 240° C. to 360° C. (inclusive).

10 Claims, 2 Drawing Sheets

CATALYST FOR ISOBUTYLENE PRODUCTION AND METHOD FOR PRODUCING ISOBUTYLENE

TECHNICAL FIELD

The present invention relates to a catalyst used when isobutylene is produced by a dehydration reaction of isobutanol. In addition, the invention relates to a method for producing isobutylene using the catalyst, and particularly to a method for producing isobutylene from biomass-derived isobutanol.

BACKGROUND ART

Isobutylene is one of the important chemical raw materials that are converted into ethyl tert-butyl ether (ETBE), paraxylene, methyl methacrylate (MMA), and the like. Among these, for example, MMA is a substance with significantly high utility value as a raw material for polymethyl methacrylate that is useful as a transparent resin. There is a method of synthesizing this MMA by using isobutylene as a starting material, as one of methods for producing the MMA.

Isobutylene as a raw material for MMA is obtained by extracting isobutylene as tert-butanol from the spent BB, which is a residue obtained by the fractional distillation of butadiene from the C4 fraction obtained by naphtha cracking, by a hydration reaction using an acid catalyst and dehydrating the extracted isobutylene. In addition, there is also a method in which methyl tert-butyl ether is once synthesized from isobutylene in the spent BB and methanol and is then decomposed. Such a conventional method for producing isobutylene uses petroleum as a raw material. Thus, the development of a novel method for producing isobutylene which does not depend on petroleum is desired in the recent situation that the depletion of petroleum is concerned.

Further, carbon dioxide generated at the time of burning petroleum is considered as a cause of global warming. In this regard, a biorefinery technology has attracted the worldwide attention as an energy and chemical producing technology from biomass of a renewable resource. The biorefinery is to produce a synthesis gas, saccharides such as glucose, and aromatic compounds such as lignin by the gasification, saccharification, and extraction of various kinds of biomass and to produce energy and chemicals by converting them in various ways. Examples of the product which is produced by the biorefinery include ethanol, butanol, and diesel oil as energy. In chemicals, it is possible to produce a significantly great number of chemicals by the derivation from key compounds (platform compounds) such as saccharide-derived succinic acid, 3-hydroxypropionic acid, and aspartic acid proposed by the US Department of Energy.

Meanwhile, it is known that isobutanol can also be produced by fermenting glucose, and isobutanol is mentioned as one of the biomass-derived raw materials. For example, it is described in Patent Literature 1, Patent Literature 2, Patent Literature 3, Patent Literature 4, Patent Literature 5, and Non-Patent Literature 1 that isobutanol can be produced by dehydrating isobutanol.

CITATION LIST

Patent Literature

Patent Literature 1: WO 2011/085223 A
Patent Literature 2: JP 4-247043 A
Patent Literature 3: JP 2013-506717 A
Patent Literature 4: JP 2013-516487 A
Patent Literature 5: JP 2013-522270 A

Non-Patent Literature

Non-Patent Literature 1: Topics in Catalysis, 53 (2010) 1224-1230

SUMMARY OF THE INVENTION

Problem to be Solved by the Invention

Isobutylene is produced through the dehydration of isobutanol by using, as a catalyst for dehydration, γ-alumina or zeolite in Patent Literature 1, Patent Literature 3, Patent Literature 4, and Patent Literature 5, γ-alumina in Non-Patent Literature 1, and γ-alumina containing silica in Patent Literature 2. However, the selectivity to isobutylene in gas components after the reaction is not always sufficient.

In order to suppress the production cost of isobutylene, it is necessary to decrease the used amount of the catalyst with respect to the treated amount of isobutanol necessary for obtaining desired isobutylene or to advance the dehydration reaction at higher selectivity. In addition, it is necessary to advance the dehydration reaction at high reaction efficiency and high selectivity in the same manner as above in order to efficiently utilize the raw material for the purpose of decreasing the environmental burden.

The invention has been made to solve such a problem. An object of the invention is to provide a catalyst for dehydration with which isobutylene can be produced at a high conversion and high selectivity in a method for producing isobutylene by a dehydration reaction of isobutanol. In addition, another object of the invention is to provide a method for producing isobutylene from isobutanol at a high conversion and high selectivity.

Means for Solving Problem

The object is achieved by a catalyst for dehydration used for producing isobutylene by a dehydration reaction of isobutanol, the catalyst for dehydration having a BET specific surface area, which is calculated from $N_2$ adsorption/desorption isotherms, within a range of from 210 $m^2/g$ to 350 $m^2/g$.

In addition, the object is achieved by a method for producing isobutylene by using the catalyst for dehydration filled in a reactor through a dehydration reaction of isobutanol.

The catalyst for dehydration is preferably at least one catalyst selected from alumina, silica alumina, zeolite, and solid phosphoric acid, more preferably contains alumina, and is particularly preferably alumina. Further, when isobutylene is produced by the dehydration reaction of isobutanol, a concentration of isobutanol in a reaction gas to be supplied into the reactor filled with the catalyst for dehydration is preferably 20% by volume or more, more preferably 40% by volume or more, and further preferably 60% by volume or more. In addition, a temperature of a catalyst layer in the reactor in which the dehydration reaction of isobutanol is performed is preferably from 230° C. to 370° C. and more preferably from 240° C. to 360° C.

Effect of the Invention

According to the invention, in the method for producing isobutylene by the dehydration reaction of isobutanol, it is possible to produce isobutylene at a higher conversion and high selectivity. Further, the invention can produce isobutylene at high selectivity particularly by using biomass-derived isobutanol as a starting material, and thus the invention is also useful from the viewpoint of environmental protection.

MODE(S) FOR CARRYING OUT THE INVENTION

A catalyst for dehydration of the invention is used in a method for producing isobutylene by a dehydration reaction of isobutanol. Isobutanol that is a starting material is not particularly limited. However, it is preferable to use biomass-derived isobutanol from the viewpoint of environmental protection or the like.

Biomass-derived isobutanol is one that is purified from an organic compound obtained through a fermentation process using a fermentable saccharide of biomass, or is isobutanol that is obtained by a process including any one or more of catalytic chemical conversion or thermochemical conversion of biomass. Biomass is largely divided into those derived from resource crops and those derived from waste. The biomass derived from resource crops are, for example, food crops, wood, and flowering plants. On the other hand, examples of the biomass derived from waste include food waste, sludge such as sewage, livestock excreta, and waste paper.

The catalyst for dehydration of the invention is a catalyst for dehydration such as acid catalyst, and specific examples thereof include alumina, silica alumina, zeolite, and solid phosphoric acid. Two or more kinds of these catalysts may be concurrently used. It is preferable to use alumina particularly from the viewpoint of the selectivity to isobutylene.

The crystal morphology of alumina is not particularly limited. Specific examples thereof include various aluminas such as α-alumina, β-alumina, γ-alumina, σ-alumina, and alumina hydrate. Two or more kinds of these aluminas may be concurrently used. In the case of concurrently using two or more kinds of alumina, aluminas having different crystal morphologies may be mixed together or may have a crystal state of a mixed phase, and they are not particularly limited. A catalyst containing γ-alumina is preferable particularly from the viewpoint of a conversion of isobutanol.

Alumina may be produced by a known method, and the production method thereof is not particularly limited. For example, alumina can be easily produced by a thermal decomposition method, a precipitation method, a deposition method, a kneading method, or a method which concurrently uses these methods. Examples of the raw material for alumina include materials to produce alumina or alumina hydrate by heating or hydrolysis such as nitrate, acetate, alkoxide, sulfate, chloride, alkali aluminate, and alum. Examples of the alkali used in the hydrolysis reaction include caustic alkali, alkali carbonate, ammonia water, and ammonium carbonate.

Alumina obtained by the method as described above may be used by being molded as necessary. For example, in the case of a gas phase fixed bed reaction, it is preferable to determine the shape of a molded body in consideration of a pressure loss or diffusion of gas in a reactor. Further, it is preferable to determine the shape of the molded body in consideration of reaction conditions or mass transfer in either of a gas phase fluidized bed reaction or a liquid phase reaction. Examples of the method for molding alumina include a method of molding alumina into an arbitrary shape such as a spherical shape, a ring shape, a cylindrical shape, or a star shape by using a molding machine for powder such as a tablet molding machine, an extrusion molding machine, or a tumbling granulator. The catalyst thus obtained may be ground so as to be used as a powder. An additive may be mixed with alumina before being molded as necessary. In addition, the BET specific surface area of alumina can be adjusted by changing temperature at which an alumina precursor is calcined. Thus, this makes it possible to adjust the BET specific surface area of the catalyst. The calcination temperature of the alumina precursor is preferably 400 to 1200° C. The BET specific surface area of alumina is increased by lowering the calcination temperature, and the BET specific surface area of alumina is decreased by increasing the calcination temperature.

The BET specific surface area of typical alumina is known to be 100 to 350 $m^2/g$ Regarding the relation of the BET specific surface area of alumina and performance as the catalyst for dehydration, it is considered that alumina having a BET specific surface area larger than 175 $m^2/g$ promotes the generation of linear butenes and decreases the selectivity to isobutylene. However, the present inventors have found that alumina having a BET specific surface area within a range of from 210 $m^2/g$ to 350 $m^2/g$ does not promote the generation of linear butenes and provides isobutylene at a high yield, and completed the present invention accordingly. The BET specific surface area of the catalyst for dehydration used in the invention as calculated from $N_2$ adsorption/desorption isotherms is within a range of from 210 $m^2/g$ to 350 $m^2/g$. The lower limit of the BET specific surface area is preferably 215 $m^2/g$ or more, more preferably 220 $m^2/g$ or more, further preferably 225 $m^2/g$, and particularly preferably 230 $m^2/g$ or more. In a case where the BET specific surface area is less than 210 $m^2/g$, sufficient selectivity to isobutylene or a sufficient conversion of isobutanol is not obtained, and productivity of isobutylene is lowered. Since an expensive structure directing agent or the like is necessary for forming uniform fine pores in the case of alumina having a BET specific surface area of more than 350 $m^2/g$, the alumina is not preferable as a catalyst to be industrially used. Incidentally, the BET specific surface area is a value measured by using TriStar 3000 (trade name, manufactured by SHIMADZU CORPORATION).

Alumina used as the catalyst for dehydration in the invention may contain a compound other than alumina. However, the content of $SiO_2$ in the catalyst for dehydration is preferably 1.0% by mass or less, more preferably 0.75% by mass or less, and further preferably 0.50% by mass or less. In a case where the catalyst for dehydration contains $SiO_2$, sufficient selectivity to isobutylene is not obtained in some cases. In addition, the content of $Na_2O$ in the catalyst for dehydration is preferably 0.2% by mass or less, more preferably 0.15% by mass or less, and particularly preferably 0.1% by mass or less. In a case where the catalyst for dehydration contains $Na_2O$, a sufficient conversion of isobutanol is not obtained in some cases.

The dehydration reaction of isobutanol may be conducted in either of a liquid phase or a gas phase. It is possible to utilize the form of gas phase reaction represented by the fixed bed and the fluidized bed in the case of conducting the reaction in a gas phase. Hereinafter, a case where the reaction is conducted in a gas phase will be described, but the invention is not limited thereto.

It is preferable to supply isobutanol as a raw material into the reactor by being evaporated in advance. An evaporator for evaporating the raw material is not particularly limited. For example, it is possible to use various kinds of evaporators such as a jacket type, a natural circulation horizontal tube type, a natural circulation immersing tube type, a natural circulation vertical short tube type, a long vertical tube rising film type, a horizontal tube falling film type, a forced circulation horizontal tube type, a forced circulation vertical tube type, and a coil type. In addition, it is also possible to employ a method in which a heating coil is simply wound around a raw material supply pipe and a raw material, which moves in the raw material supply pipe, is evaporated in the raw material supply pipe before being introduced into the reactor and is supplied into the reactor in a gaseous state. Further, the evaporator is not particularly limited in a case where a component other than the raw material is evaporated to be supplied into the reactor as well. The temperature for gasification is preferably 120 to 400° C., and the pressure is preferably 1 MPa as an atmospheric pressure town absolute pressure.

In the case of supplying isobutanol as a raw material into the reactor, the concentration of isobutanol in the reaction gas can be adjusted by using a diluent gas. The kind of the diluent gas is not particularly limited. For example, oxygen can be used as a diluent gas in a concentration which is out of the explosive range and in which a side reaction is not significantly promoted. In addition, hydrogen can be used as a diluent gas in a concentration in which a side reaction is not significantly promoted in the concentration range in which hydrogen can be safely operated. Further, it is possible to suitably use one or more kinds selected from the group consisting of nitrogen, helium, neon, krypton, xenon, radon, argon, methane, ethane, propane, butane, isobutane, carbon monoxide, carbon dioxide, nitrogen monoxide, nitrogen dioxide, nitrous oxide, dinitrogen trioxide, dinitrogen tetraoxide, dinitrogen pentaoxide, and water vapor as a diluent gas. The concentration of isobutanol in the raw material gas to be supplied into the reactor is preferably 20% by volume or more, more preferably 40% by volume or more, and further preferably 60% by volume or more. When the concentration of the raw material is lower than the aforementioned range, sufficient selectivity to isobutylene is not obtained in some cases.

The reaction pressure during the dehydration reaction of isobutanol is not particularly limited, but is preferably 1 MPa as an atmospheric pressure to an absolute pressure. When the reaction pressure is measured, it is desirable to monitor the reaction pressure of a catalyst layer. However, in a case where it is difficult to attach a sensor into the catalyst layer because of the process, a pressure value measured by a pressure sensor installed at an inlet of the reactor may be considered as the reaction pressure. In the invention, the "reaction pressure" is defined as a pressure value of the pressure sensor installed at a position at which the influence of pressure loss is negligible with respect to the pressure at the inlet of the reactor.

It is preferable that the reaction temperature (the temperature in the catalyst layer during the reaction) is selected within a range of from 108 to 418° C. From the viewpoint of sufficiently obtaining the effect of the invention, the lower limit of the reaction temperature is more preferably 230° C. or higher and further preferably 240° C. or higher. Meanwhile, the upper limit of the reaction temperature is more preferably 360° C. or lower and further preferably 350° C. or lower. When the reaction temperature is suitably low, the reaction rate of the isomerization reaction is suppressed and thus the selectivity to isobutylene that is a target product is improved. On the other hand, when the reaction temperature is suitably high, it is less required to increase the amount of the catalyst or to lower the supply rate of the raw material gas, which is advantageous from the viewpoint of cost or productivity as well. The dehydration reaction of isobutanol is an endothermic reaction, and a method for controlling the reaction temperature is not particularly limited. Herein, the "reaction temperature" is defined as the lowest temperature among temperatures in the catalyst layer which can be confirmed after the catalyst layer is in a steady state. Therefore, it is desirable to increase the points of measurement or to continuously measure the temperature in the catalyst filling direction in a case where there is a temperature distribution in the catalyst layer.

According to the invention described above, it is possible to produce isobutylene at a sufficient conversion and sufficient selectivity by the dehydration reaction of isobutanol.

EXAMPLES

Hereinafter, the invention will be described in detail by means of Examples of the invention. However, the invention is not limited to these Examples.

Analysis of the raw material gas and the product was conducted by gas chromatography. The conversion of isobutanol and the selectivity to isobutylene to be generated are respectively defined as follows.

Conversion (%) of isobutanol=(b/a)×100
Selectivity (%) to isobutylene=(c/d)×100
a=the number of moles of isobutanol supplied
b=the number of moles of isobutanol reacted
c=the number of moles of isobutylene generated
d=the total number of moles of reaction product (isobutylene, isobutane, 1-butene, cis-2-butene, and trans-2-butene) detected by gas chromatography In addition, the weight hourly space velocity (WHSV) of isobutanol per unit time is defined as follows.

WHSV of isobutanol (1/hr)=e/f e=the supplied amount of isobutanol per unit time (g/hr)
f=the mass of catalyst used (g)

The BET specific surface area calculated from $N_2$ adsorption/desorption isotherms was measured by using TriStar 3000 (trade name, manufactured by SHIMADZU CORPORATION).

Example 1

The catalyst for dehydration was filled in a vertical tubular reaction tube having an inner diameter of 0.75 cm and a length of 40 cm to form a catalyst layer. As the catalyst for dehydration, 0.1412 g of crushed body of alumina (alumina having a γ-alumina phase (γ phase) as a main component of a crystalline layer, particle diameter: 800 to 1190 μm, BET specific surface area: 267 m²/g, hereinafter, referred to as the "catalyst A") molded in a cylindrical pellet shape (diameter: 1.6 mm) was used. Regarding a reactor, the temperature in the catalyst layer was adjusted by using an electric furnace such that the temperature in the catalyst layer reached a predetermined temperature. In addition, the reaction pressure was adjusted by using a back pressure valve such that the reaction pressure reached a predetermined pressure. Then, isobutanol (manufactured by NAC-ALAI TESQUE, INC., purity: 99.5% by mass, specific gravity: 0.803 g/mL) of the raw material was supplied into an evaporator set 200° C. while the flow rate thereof was adjusted to 0.069 mL/min by using a double plunger pump, and then isobutanol was evaporated. The nitrogen gas as a diluent gas was supplied into the evaporator at a flow rate of 150 mL (standard state)/min by using a mass flow meter and supplied into the reactor together with the evaporated isobutanol. At this time, the concentration of isobutanol in the raw material gas supplied to the catalyst layer was 10.0% by volume.

The reaction evaluation was started after 5 minutes passed from the state where the temperature in the catalyst layer and the reaction pressure were respectively stabilized with fluctuations in a predetermined temperature ±0.5° C. and a predetermined pressure ±0.5 kPa. The lowest temperature in the catalyst layer during the reaction (reaction temperature) was 340° C. The gas at the outlet side of the reactor was collected after the reaction reached the steady state, and subjected to the quantification of isobutylene, isobutane, 1-butene, cis-2-butene, and trans-2-butene by using gas chromatography. In addition, the reaction gas discharged from the outlet side of the reactor was trapped by using ice-cold acetonitrile and subjected to the quantification of isobutanol by using gas chromatography. A pressure gauge for measuring the reaction pressure was installed between the evaporator and the inlet of the reactor. Incidentally, it was confirmed that the pressure loss from the evaporator to the inlet of the reactor was so small as to be negligible in all the flow rate ranges under the conditions of Examples 1 to 18 and Comparative Examples 1 to 11, including this Example. The WHSV was 23.5 h$^{-1}$, and the reaction pressure was 108 kPa as the absolute pressure.

Example 2

The reaction and the measurement were conducted in the same manner as in Example 1, except that 0.1015 g of crushed body of alumina (alumina having a γ-alumina phase (γ phase) as a main component of a crystalline layer, particle diameter: 800 to 1190 μm, BET specific surface area: 243 m$^2$/g, hereinafter, referred to as the "catalyst B") molded in a cylindrical pellet shape (diameter: 1.6 mm) was used as the catalyst for dehydration. The reaction temperature, the reaction pressure, the WHSV, the conversion of isobutanol, the selectivity to isobutylene, and the yield of isobutylene are presented in Table 1.

Comparative Example 1

The reaction and the measurement were conducted in the same manner as in Example 1, except that 0.1317 g of crushed body of alumina (alumina having a γ phase as a main component of a crystalline layer, particle diameter: 800 to 1190 μm, BET specific surface area: 200 m$^2$/g, hereinafter, referred to as the "catalyst C") molded in a cylindrical pellet shape (diameter: 1.6 mm) was used as the catalyst for dehydration. The reaction conditions and the measurement results are presented in Table 1.

Comparative Example 2

The reaction and the measurement were conducted in the same manner as in Example 1, except that 0.1313 g of crushed body of alumina (alumina having a γ phase as a main component of a crystalline layer, particle diameter: 800 to 1190 μm, BET specific surface area: 195 m$^2$/g, hereinafter, referred to as the "catalyst D") molded in a cylindrical pellet shape (diameter: 1.6 mm) was used as the catalyst for dehydration. The reaction conditions and the measurement results are presented in Table 1.

Comparative Example 3

The reaction and the measurement were conducted in the same manner as in Example 1, except that 0.2824 g of crushed body of alumina (alumina having a γ phase as a main component of a crystalline layer, particle diameter: 800 to 1190 μm, BET specific surface area: 162 m$^2$/g, hereinafter, referred to as the "catalyst E") molded in a cylindrical pellet shape (diameter: 1.6 mm) was used as the catalyst for dehydration. The reaction conditions and the measurement results are presented in Table 1.

Comparative Example 4

The reaction and the measurement were conducted in the same manner as in Example 1, except that 0.4836 g of crushed body of alumina (alumina having a γ phase as a main component of a crystalline layer, particle diameter: 800 to 1190 μm, BET specific surface area: 105 m$^2$/g, hereinafter, referred to as the "catalyst F") molded in a cylindrical pellet shape (diameter: 1.6 mm) was used as the catalyst for dehydration. The reaction conditions and the measurement results are presented in Table 1.

Comparative Example 5

The reaction and the measurement were conducted in the same manner as in Example 1, except that 0.8830 g of crushed body of alumina (alumina having a γ phase as a main component of a crystalline layer, particle diameter: 800 to 1190 μm, BET specific surface area: 69 m$^2$/g, hereinafter, referred to as the "catalyst G") molded in a cylindrical pellet shape (diameter: 3.0 mm) was used as the catalyst for dehydration. The reaction conditions and the measurement results are presented in Table 1.

Figure 1:
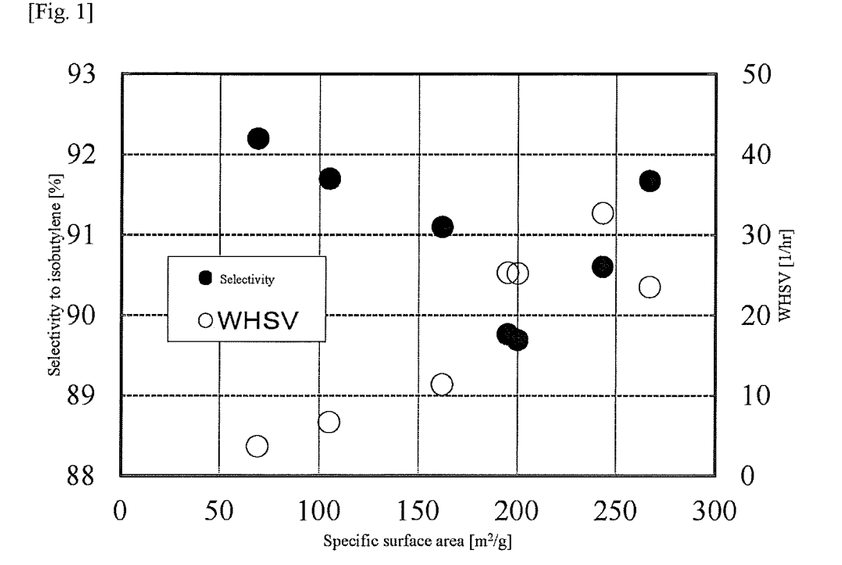
FIG. 1 is a graph showing a relation between a BET specific surface area and the selectivity to isobutylene in Examples 1 and 2 and Comparative Examples 1 to 5.

The above Examples 1 and 2 and Comparative Examples 1 to 5 correspond to examples in which the concentration of isobutanol in the raw material gas is 10.0% by volume and the reaction temperature is 340° C. The relation between the BET specific surface area and the selectivity to isobutylene of the catalyst for dehydration based on these examples is illustrated in FIG. 1.

Example 3

The reaction and the measurement were conducted in the same manner as in Example 1, except that the amount of the catalyst A was changed to 0.1921 g and the flow rates of isobutanol and the nitrogen gas were changed to 0.263 mL/min and 16 mL (standard state)/min, respectively. The concentration of isobutanol in the raw material gas supplied to the catalyst layer was 79.9% by volume. The reaction conditions and the measurement results are presented in Table 2.

Example 4

The reaction and the measurement were conducted in the same manner as in Example 1, except that the amount of the catalyst B was changed to 0.1907 g and the flow rates of isobutanol and the nitrogen gas were changed to 0.263 mL/min and 16 mL (standard state)/min, respectively. The concentration of isobutanol in the raw material gas supplied to the catalyst layer was 79.9% by volume. The reaction conditions and the measurement results are presented in Table 2.

Comparative Example 6

The reaction and the measurement were conducted in the same manner as in Example 1, except that the amount of the catalyst C was changed to 0.2216 g and the flow rates of isobutanol and the nitrogen gas were changed to 0.263 mL/min and 16 mL (standard state)/min, respectively. The concentration of isobutanol in the raw material gas supplied to the catalyst layer was 79.9% by volume. The reaction conditions and the measurement results are presented in Table 2.

Comparative Example 7

The reaction and the measurement were conducted in the same manner as in Example 1, except that the amount of the catalyst D was changed to 0.2521 g and the flow rates of isobutanol and the nitrogen gas were changed to 0.263 mL/min and 16 mL (standard state)/min, respectively. The concentration of isobutanol in the raw material gas supplied to the catalyst layer was 79.9% by volume. The reaction conditions and the measurement results are presented in Table 2.

Comparative Example 8

The reaction and the measurement were conducted in the same manner as in Example 1, except that the amount of the catalyst E was changed to 0.2741 g and the flow rates of isobutanol and the nitrogen gas were changed to 0.218 mL/min and 13 mL (standard state)/min, respectively. The concentration of isobutanol in the raw material gas supplied to the catalyst layer was 79.7% by volume. The reaction conditions and the measurement results are presented in Table 2.

Comparative Example 9

The reaction and the measurement were conducted in the same manner as in Example 1, except that the amount of the catalyst F was changed to 0.8207 g and the flow rates of isobutanol and the nitrogen gas were changed to 0.263 mL/min and 16 mL (standard state)/min, respectively. The concentration of isobutanol in the raw material gas supplied to the catalyst layer was 79.9% by volume. The reaction conditions and the measurement results are presented in Table 2.

Comparative Example 10

The reaction and the measurement were conducted in the same manner as in Example 1, except that the amount of the catalyst G was changed to 1.504 g and the flow rates of isobutanol and the nitrogen gas were changed to 0.218 mL/min and 13 mL (standard state)/min, respectively. The concentration of isobutanol in the raw material gas supplied to the catalyst layer was 79.7% by volume. The reaction conditions and the measurement results are presented in Table 2.

Figure 2:
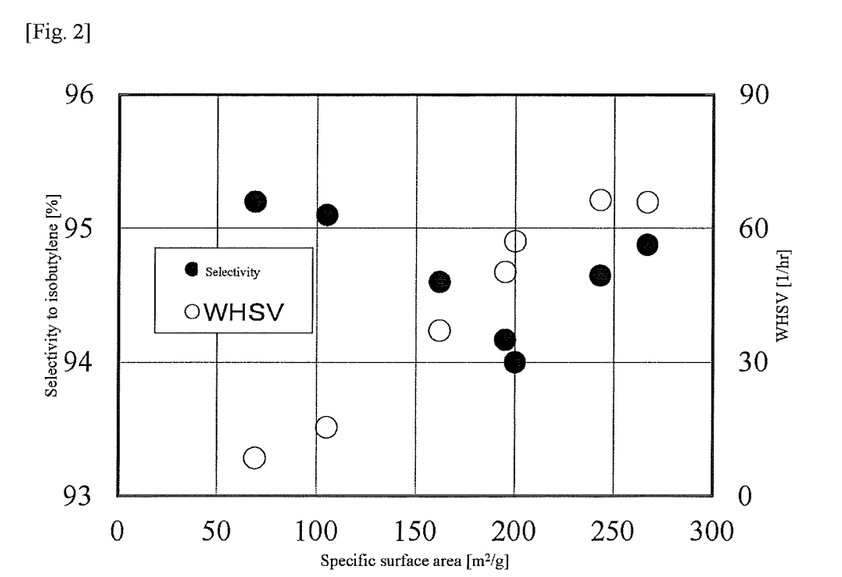
FIG. 2 is a graph showing a relation between a BET specific surface area and the selectivity to isobutylene in Examples 3 and 4 and Comparative Examples 6 to 10.

The above Examples 3 and 4 and Comparative Examples 6 to 10 correspond to examples in which the concentration of isobutanol in the raw material gas is 79.7 to 79.9% by volume and the reaction temperature is 340° C. The relation between the BET specific surface area and the selectivity to isobutylene of the catalyst for dehydration based on these examples is illustrated in FIG. 2.

Example 5

The catalyst for dehydration was filled in a vertical tubular reaction tube having an inner diameter of 1.6 cm and a length of 50 cm. As the catalyst for dehydration, 24.00 g of the catalyst B was used. Then, isobutanol (manufactured by NACALAI TESQUE, INC., purity: 99.5% by mass, specific gravity: 0.803 g/mL) was supplied into an evaporator set to 200° C. while the flow rate thereof was adjusted to 0.536 mL/min by using a double plunger pump, and then isobutanol was evaporated. The nitrogen gas as a diluent gas was supplied into the evaporator at a flow rate of 55 mL (standard state)/min by using a mass flow meter and supplied into the reactor together with the evaporated isobutanol. At this time, the concentration of isobutanol in the raw material gas supplied to the catalyst layer was 70.3% by volume. The reaction conditions and the measurement results are presented in Table 3.

Comparative Example 11

The reaction and the measurement were conducted in the same manner as in Example 5, except that 29.57 g of the catalyst F was used. The reaction conditions and the measurement results are presented in Table 3.

Example 6

The reaction and the measurement were conducted in the same manner as in Example 1, except that 0.1015 g of the catalyst B was used and the flow rates of isobutanol and the nitrogen gas were changed to 0,092 ml/min and 200 ml (standard)/min, respectively. The concentration of isobutanol in the raw material gas supplied to the catalyst layer was 10.0% by volume. The reaction conditions and the measurement results are presented in Table 4.

Example 7

The reaction and the measurement were conducted in the same manner as in Example 1, except that 0.2508 g of the catalyst B was used and the flow rates of isobutanol and the nitrogen gas were changed to 0.270 ml/min and 95 ml (standard)/min, respectively. The concentration of isobutanol in the raw material gas supplied to the catalyst layer was 40.0% by volume. The reaction conditions and the measurement results are presented in Table 4.

Example 8

The reaction and the measurement were conducted in the same manner as in Example 1, except that 0.2508 g of the catalyst B was used and the flow rates of isobutanol and the nitrogen gas were changed to 0.270 ml/min and 42 ml (standard)/min, respectively. The concentration of isobutanol in the raw material gas supplied to the catalyst layer was 60.2% by volume. The reaction conditions and the measurement results are presented in Table 4.

Example 9

The reaction and the measurement were conducted in the same manner as in Example 1, except that 0.2508 g of the catalyst B was used and the flow rates of isobutanol and the nitrogen gas were changed to 0.270 ml/min and 0 ml (standard)/min, respectively. The concentration of isobutanol in the raw material gas supplied to the catalyst layer was 100% by volume. The reaction conditions and the measurement results are presented in Table 4.

Figure 3:
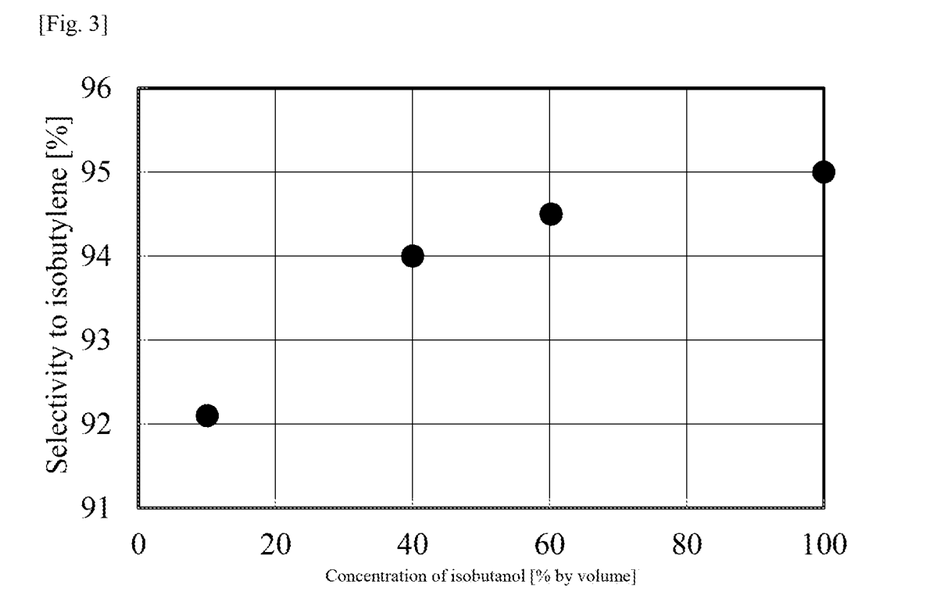
FIG. 3 is a graph showing a relation between a concentration of isobutanol in a raw material gas and the selectivity to isobutylene in Example 4 and 6 to 9.

The relation between the concentration of isobutanol in the raw material gas and the selectivity to isobutylene based on the above Examples 4 and 6 to 9 is illustrated in FIG. 3.

Example 10

The reaction and the measurement were conducted in the same manner as in Example 5, except that 20.79 g of the molded body (cylindrical pellet shape (diameter: 3.0 mm)) of the catalyst B was used and the flow rates of isobutanol and the nitrogen gas were changed to 0.965 mL/min and 101 mL (standard state)/min, respectively. The concentration of isobutanol in the raw material gas supplied to the catalyst layer was 70.0% by volume. The reaction conditions and the measurement results are presented in Table 5.

Examples 11 to 18

Figure 4:
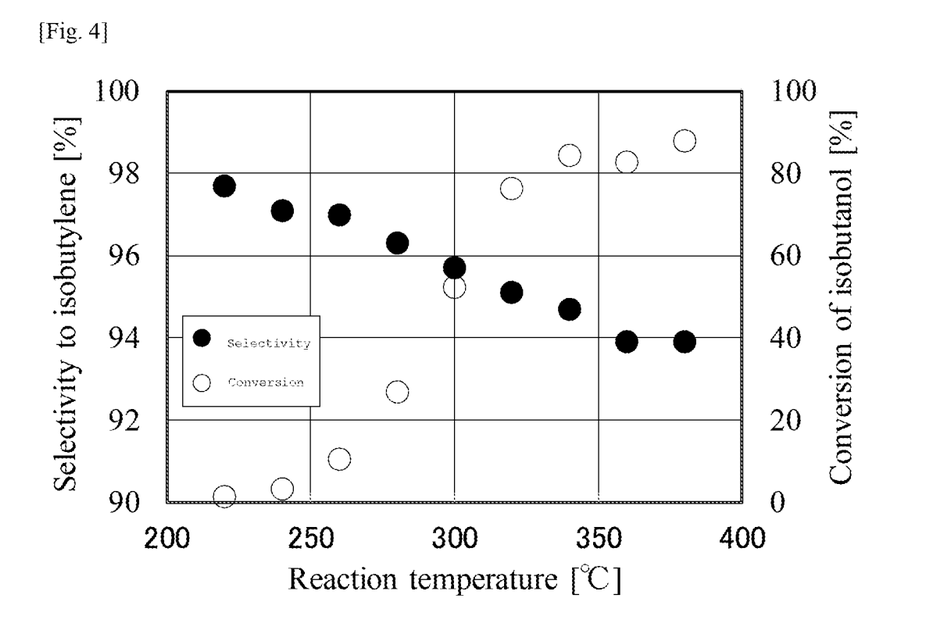
FIG. 4 is a graph showing a relation between a reaction temperature, a conversion of isobutanol, and the selectivity to isobutylene in Examples 10 to 18.

The reaction and the measurement were conducted in the same manner as in Example 5, except that 2.904 g of the molded body (cylindrical pellet shape (diameter: 3.0 mm)) of the catalyst B was used and the flow rates of isobutanol and the nitrogen gas were changed to 0.487 mL/min and 50 mL (standard state)/min, respectively. The concentration of isobutanol in the raw material gas supplied to the catalyst layer was 70.2% by volume. The reaction conditions and the measurement results are presented in Table 5. The relation among the reaction temperature, the conversion of isobutanol, and the selectivity to isobutylene based on the above Examples 10 to 18 is illustrated in FIG. 4.

TABLE 1

| No. | Catalyst | Specific surface area [m$^2$/g] | Reaction temperature [° C.] | Reaction pressure [kPaA] | Mass of catalyst [g] | WHSV [l/hr] | Raw material gas composition [% by volume] | |
|---|---|---|---|---|---|---|---|---|
| | | | | | | | Isobutanol | Nitrogen |
| Example 1 | A | 267 | 340 | 108 | 0.1412 | 23.5 | 10.0 | 90.0 |
| Example 2 | B | 243 | 340 | 109 | 0.1015 | 32.7 | 10.0 | 90.0 |
| Comparative Example 1 | C | 200 | 340 | 110 | 0.1317 | 25.2 | 10.0 | 90.0 |
| Comparative Example 2 | D | 195 | 340 | 109 | 0.1313 | 25.3 | 10.0 | 90.0 |
| Comparative Example 3 | E | 162 | 340 | 109 | 0.2824 | 11.4 | 10.0 | 90.2 |
| Comparative Example 4 | F | 105 | 340 | 109 | 0.4836 | 6.7 | 10.0 | 90.2 |
| Comparative Example 5 | G | 69 | 340 | 109 | 0.8830 | 3.7 | 10.0 | 90.2 |

| No. | Conversion [%] | Selectivity [%] | | | | | Yield of isobutylene [%] |
|---|---|---|---|---|---|---|---|
| | | Isobutylene | Isobutane | 1-Butene | Cis-2-butene | Trans-2-butene | |
| Example 1 | 98.0 | 91.7 | 0.0 | 3.2 | 3.9 | 1.2 | 89.8 |
| Example 2 | 96.1 | 90.6 | 0.0 | 3.6 | 4.4 | 1.4 | 87.1 |
| Comparative Example 1 | 97.6 | 89.7 | 0.0 | 3.6 | 4.7 | 2.0 | 87.6 |
| Comparative Example 2 | 95.3 | 89.8 | 0.0 | 3.7 | 4.7 | 1.8 | 85.5 |
| Comparative Example 3 | 99.7 | 91.1 | 0.1 | 3.5 | 3.9 | 1.4 | 90.8 |
| Comparative Example 4 | 98.5 | 91.7 | 0.1 | 3.4 | 3.5 | 1.3 | 90.3 |
| Comparative Example 5 | 99.3 | 92.2 | 0.1 | 3.4 | 3.1 | 1.2 | 91.6 |

TABLE 2

| No. | Catalyst | Specific surface area [m$^2$/g] | Reaction temperature [° C.] | Reaction pressure [kPaA] | Mass of catalyst [g] | WHSV [l/hr] | Raw material gas composition [% by volume] | |
|---|---|---|---|---|---|---|---|---|
| | | | | | | | Isobutanol | Nitrogen |
| Example 3 | A | 267 | 340 | 106 | 0.1921 | 65.9 | 79.9 | 20.1 |
| Example 4 | B | 243 | 340 | 109 | 0.1907 | 66.4 | 79.9 | 20.1 |
| Comparative Example 6 | C | 200 | 340 | 107 | 0.2216 | 57.1 | 79.9 | 20.1 |
| Comparative Example 7 | D | 195 | 340 | 107 | 0.2521 | 50.2 | 79.9 | 20.1 |
| Comparative Example 8 | E | 162 | 340 | 107 | 0.2741 | 37.1 | 79.7 | 20.1 |
| Comparative Example 9 | F | 105 | 340 | 107 | 0.8207 | 15.4 | 79.9 | 20.1 |
| Comparative Example 10 | G | 69 | 340 | 107 | 1.504 | 8.5 | 79.7 | 20.0 |

TABLE 2-continued

|  | Conversion | Selectivity [%] | | | | | Yield of |
| --- | --- | --- | --- | --- | --- | --- | --- |
| No. | [%] | Isobutylene | Isobutane | 1-Butene | Cis-2-butene | Trans-2-butene | isobutylene [%] |
| Example 3 | 73.6 | 94.9 | 0.1 | 2.0 | 2.3 | 0.6 | 69.8 |
| Example 4 | 74.3 | 74.6 | 0.1 | 2.1 | 2.5 | 0.7 | 70.3 |
| Comparative Example 6 | 79.0 | 94.0 | 0.2 | 2.2 | 2.8 | 0.8 | 74.3 |
| Comparative Example 7 | 76.3 | 94.2 | 0.2 | 2.2 | 2.7 | 0.8 | 71.8 |
| Comparative Example 8 | 72.5 | 94.6 | 0.2 | 2.4 | 2.1 | 0.7 | 68.6 |
| Comparative Example 9 | 76.4 | 99.1 | 0.1 | 2.0 | 2.2 | 0.6 | 72.7 |
| Comparative Example 10 | 82.1 | 95.2 | 0.2 | 2.3 | 1.6 | 0.8 | 78.2 |

TABLE 3

| No. | Catalyst | Specific surface area [m²/g] | Reaction temperature [° C.] | Reaction pressure [kPaA] | Mass of catalyst [g] | WHSV [l/hr] | Raw material gas composition [% by volume] | |
| --- | --- | --- | --- | --- | --- | --- | --- | --- |
|  |  |  |  |  |  |  | Isobutanol | Nitrogen |
| Example 5 | B | 243 | 209 | 104 | 24.00 | 1.1 | 70.3 | 29.7 |
| Comparative Example 11 | F | 105 | 290 | 104 | 29.57 | 0.9 | 70.3 | 29.7 |

| No. | Conversion [%] | Selectivity [%] | | | | | Yield of isobutylene [%] |
| --- | --- | --- | --- | --- | --- | --- | --- |
|  |  | Isobutylene | Isobutane | 1-Butene | Cis-2-butene | Trans-2-butene |  |
| Example 5 | 99.3 | 95.5 | 0.1 | 1.7 | 1.9 | 0.8 | 94.8 |
| Comparative Example 11 | 48.7 | 95.3 | 0.1 | 1.8 | 1.8 | 1.0 | 46.4 |

TABLE 4

| No. | Catalyst | Reaction temperature [° C.] | Reaction pressure [kPaA] | WHSV [l/hr] | Mass of catalyst [g] | Raw material gas composition [% by volume] | | Conversion [%] |
| --- | --- | --- | --- | --- | --- | --- | --- | --- |
|  |  |  |  |  |  | Isobutanol | Nitrogen |  |
| Example 6 | B | 340 | 110 | 43.6 | 0.1015 | 10.0 | 90.0 | 85.8 |
| Example 7 | B | 340 | 108 | 50.2 | 0.2508 | 40.0 | 60.0 | 88.2 |
| Example 8 | B | 340 | 107 | 50.2 | 0.2508 | 60.2 | 39.8 | 82.5 |
| Example 9 | B | 340 | 107 | 50.2 | 0.2508 | 100.0 | 0.0 | 81.0 |

| No. | Selectivity [%] | | | | | Yield of isobutylene [%] |
| --- | --- | --- | --- | --- | --- | --- |
|  | Isobutylene | Isobutane | 1-Butene | Cis-2-butene | Trans-2-butene |  |
| Example 6 | 92.1 | 0.0 | 3.0 | 3.8 | 1.1 | 79.0 |
| Example 7 | 94.0 | 0.2 | 2.5 | 2.5 | 0.8 | 82.9 |
| Example 8 | 94.5 | 0.2 | 2.4 | 2.2 | 0.7 | 78.0 |
| Example 9 | 95.0 | 0.2 | 2.2 | 1.9 | 0.7 | 77.0 |

TABLE 5

| No. | Catalyst | Reaction temperature [° C.] | Reaction pressure [kPaA] | WHSV [l/hr] | Mass of catalyst [g] | Raw material gas composition [% by volume] | | Conversion [%] |
| --- | --- | --- | --- | --- | --- | --- | --- | --- |
|  |  |  |  |  |  | Isobutanol | Nitrogen |  |
| Example 10 | B | 220 | 104 | 2.3 | 20.79 | 70.0 | 30.0 | 1.4 |
| Example 11 | B | 240 | 104 | 8.1 | 2.904 | 70.2 | 29.8 | 3.2 |
| Example 12 | B | 260 | 104 | 8.1 | 2.904 | 70.2 | 29.8 | 10.5 |
| Example 13 | B | 280 | 104 | 8.1 | 2.808 | 70.2 | 29.8 | 26.8 |

TABLE 5-continued

| | | | | | | | | |
|---|---|---|---|---|---|---|---|---|
| Example 14 | B | 300 | 104 | 8.1 | 2.908 | 70.2 | 29.8 | 52.3 |
| Example 15 | B | 320 | 104 | 8.1 | 2.902 | 70.2 | 29.8 | 76.3 |
| Example 16 | B | 340 | 104 | 8.1 | 2.902 | 70.2 | 29.8 | 84.5 |
| Example 17 | B | 360 | 104 | 8.1 | 2.907 | 70.2 | 29.8 | 82.8 |
| Example 18 | B | 380 | 104 | 8.1 | 2.907 | 70.2 | 29.8 | 88.0 |

| | Selectivity [%] | | | | | Yield of isobutylene |
|---|---|---|---|---|---|---|
| No. | Isobutylene | Isobutane | 1-Butene | Cis-2-butene | Trans-2-butene | [%] |
| Example 10 | 97.7 | 0.2 | 0.7 | 0.8 | 0.6 | 1.4 |
| Example 11 | 97.1 | 0.2 | 1.0 | 1.2 | 0.5 | 3.1 |
| Example 12 | 97.0 | 0.1 | 1.1 | 1.5 | 0.3 | 10.2 |
| Example 13 | 96.3 | 0.1 | 1.4 | 1.7 | 0.5 | 25.8 |
| Example 14 | 95.7 | 0.1 | 1.6 | 2.0 | 0.6 | 50.1 |
| Example 15 | 95.1 | 0.2 | 2.0 | 2.1 | 0.6 | 72.6 |
| Example 16 | 94.7 | 0.2 | 2.1 | 2.3 | 0.7 | 80.0 |
| Example 17 | 93.9 | 0.2 | 2.5 | 2.4 | 1.0 | 77.7 |
| Example 18 | 93.9 | 0.1 | 2.5 | 2.5 | 1.0 | 82.6 |

In Examples 1 to 5 as presented in Tables 1 to 3, it was possible to produce isobutylene at high selectivity or a high conversion. On the other hand, the selectivity or the conversion in Comparative Examples 1 to 11 was inferior to Examples 1 to 5. In addition, in Examples 6 to 9 as presented in Table 4, it was possible to produce isobutylene at high selectivity in any concentration of isobutanol. However, in Examples 8 and 9, as compared to Examples 6 and 7, it was possible to produce isobutylene at higher selectivity. Further, in Examples 10 to 18 as presented in Table 5, it was possible to produce isobutylene at high selectivity or a high conversion in any concentration of isobutanol. However, in Examples 12 to 16, as compared to Examples 10, 11, and 18, it was possible to produce isobutylene at higher selectivity or a higher conversion.

INDUSTRIAL APPLICABILITY

The isobutylene obtained by the invention is one of the important chemical raw materials that are converted into ethyl tert-butyl ether (ETBE), paraxylene, methyl methacrylate (MMA), and the like. Among these, particularly, MMA is a substance with significantly high utility value as a raw material for polymethyl methacrylate that is useful as a transparent resin.

The invention claimed is:

1. A method for producing isobutylene, the method comprising:
   carrying out a dehydration reaction of isobutanol in a reactor in the presence of a catalyst for dehydration
   wherein the catalyst for dehydration is alumina and has a BET specific surface area, which is calculated from $N_2$ adsorption/desorption isotherms, within a range of from 210 $m^2/g$ to 350 $m^2/g$, and
   wherein a concentration of isobutanol in a reaction gas supplied to said reactor is 20% by volume or more.
2. The method according to claim 1, wherein the specific surface area of the catalyst is from 215 $m^2/g$ to 350 $m^2/g$.
3. The method according to claim 1, wherein the specific surface area of the catalyst is from 220 $m^2/g$ to 350 $m^2/g$.
4. The method according to claim 1, wherein the specific surface area of the catalyst is from 225 $m^2/g$ to 350 $m^2/g$.
5. The method according to claim 1, wherein the specific surface area of the catalyst is from 230 $m^2/g$ to 350 $m^2/g$.
6. The method according to claim 1, wherein a concentration of isobutanol in a reaction gas supplied to said reactor is 40% by volume or more.
7. The method according to claim 1, wherein a concentration of isobutanol in a reaction gas supplied to said reactor is 60% by volume or more.
8. The method according to claim 1, wherein a temperature of a catalyst layer in the reactor is from 230° C. to 360° C.
9. The method according to claim 1, wherein a temperature of a catalyst layer in the reactor is from 240° C. to 350° C.
10. The method according to claim 1, wherein a content of $SiO_2$ in the catalyst is 1.0% by mass or less.

* * * * *